(12) United States Patent
Kobayashi et al.

(10) Patent No.: US 6,271,391 B1
(45) Date of Patent: Aug. 7, 2001

(54) HYDRAZIDE FIXED TO A RESIN AND DERIVATIVES THEREOF, AND A METHOD FOR SYNTHESIZING PYRAZOLONES IN SOLID PHASE

(75) Inventors: Shu Kobayashi, Tokyo; Hidekazu Oyamada, Saitama, both of (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 09/646,041
(22) PCT Filed: Mar. 12, 1999
(86) PCT No.: PCT/JP99/01222
  § 371 Date: Nov. 8, 2000
  § 102(e) Date: Nov. 8, 2000
(87) PCT Pub. No.: WO99/46238
  PCT Pub. Date: Sep. 16, 1999
(30) Foreign Application Priority Data
  Mar. 13, 1998 (JP) .................................... 10-082776
(51) Int. Cl.$^7$ ........................ C07D 231/20; C08F 220/60
(52) U.S. Cl. ........................................ 548/366.1; 528/492
(58) Field of Search ........................... 548/366.1; 528/492

(56) References Cited

U.S. PATENT DOCUMENTS 3,959,080 * 5/1976 Orth et al. .............................. 195/63

* cited by examiner

*Primary Examiner*—Robert W. Ramsuer
(74) *Attorney, Agent, or Firm*—Wenderoth, Lind & Ponack, L.L.P.

(57) ABSTRACT

Hydrazide fixed to a resin represented by the following formula:

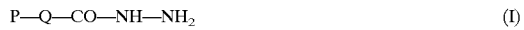

$$P-Q-CO-NH-NH_2 \quad (I)$$

where P represents a main chain of a resin polymer and Q represents a hydrocarbon side chain optionally having a substituent which may be bonded via a heteroatom, and a hydrazone derived therefrom and fixed to a resin

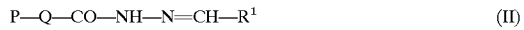

$$P-Q-CO-NH-N=CH-R^1 \quad (II)$$

are provided, and solid phase synthesis of pyrazolone is conducted using the same, thereby enabling synthesis of pyrazolones by the application of the Mannich type reaction based on the solid phase synthesis and efficient construction of libraries for various kinds of them.

3 Claims, No Drawings

HYDRAZIDE FIXED TO A RESIN AND DERIVATIVES THEREOF, AND A METHOD FOR SYNTHESIZING PYRAZOLONES IN SOLID PHASE

This application is a 371 of PCT/JP99/01222 filed Mar. 12, 1999.

1. Field of the Invention

This invention concerns a hydrazide fixed to a resin and derivatives thereof, and a method for synthesizing pyrazolones in a solid phase.

2. Related Art Statement

Solid phase synthesis methods using a resin carrier have been known so far in, for example, peptide synthesis, and the solid phase synthesis method is an effective means for synthesizing a plurality kinds of analogous group of compounds all at once, and it has been considered to apply the solid phase synthesis method also to various kinds of chemical reactions.

However, it has actually been a problem that reactions to which the method is applicable are restricted in the solid phase reaction compared with liquid phase reaction which is predominant in the chemical synthesis. In view of the prior art situation described above for the solid phase synthesis method, the inventors of the present application have studied for improving the effectiveness of the solid phase synthesis method by conducting carbon-carbon bond forming reactions which are most basic and important in the synthesis of organic compounds efficiently on a solid phase.

In particular, the inventors of the present application have found a novel method of conducting a Mannich type reaction starting from an acyl hydrazone using a catalyst and it is an important subject to establish a solid phase synthesis method capable of further improving the effectiveness of this method in view of practical use.

OBJECT AND SUMMARY OF THE INVENTION

Then, it is a subject of this invention in the present application to provide a novel technical means for realizing the Mannich type reaction as described above as a solid phase synthesis method and, more specially, to provide a method of synthesizing pyrazolones by applying the Mannich type reaction utilizing the solid phase synthesis.

For attaining the subject described above, a first invention provides a β-hydrazino ester fixed to a resin represented by the following formula (III):

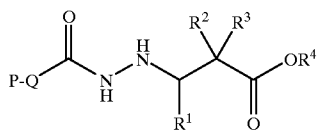

(III)

where P represents a main chain of a resin polymer, Q represents a hydrocarbon side chain optionally having a substituent which may be boned via a heteroatom, $R^1$, $R^2$, $R^3$ and $R^4$ each represents a hydrocarbon group or a heterocyclic group optionally having a substituent.

A second invention provides a production process for a β-hydrazino ester fixed to a resin as defined in the first invention, which comprises reacting a hydrazone fixed to a resin represented by the following formula:

P—Q—CO—NH—N=CH—$R^1$ (II)

where P represents a main chain of a resin, Q represents a hydrocarbon side chain optionally having a substituent which may be boned via a heteroatom and $R^1$ represents a hydrocarbon group or a heterocyclic group optionally having a substituent, with a ketene silyl acetal represented by the following formula:

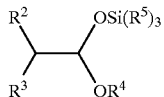

(IV)

where $R^2$, $R^3$ and $R^4$ each represents a hydrocarbon group or a heterocyclic group which may have a substituent and $R^6$ represents a hydrocarbon group.

Further, a third invention provides a method of synthesizing pyrazolones which comprises reacting a hydrazone fixed to a resin represented by the following formula:

P—Q—CO—NH—N=CH—$R^1$ (II)

where P represents a main chain of a resin, Q represents a hydrocarbon side chain optionally having a substituent which may be boned via a heteroatom and $R^1$ represents a hydrocarbon group or a heterocyclic group optionally having a substituent, with ketene silyl acetals represented by the following formula:

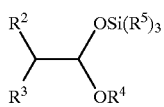

(IV)

where $R^2$, $R^3$ and $R^4$ each represents a hydrocarbon group or a heterocyclic group which may have a substituent respectively and $R^6$ represents a hydrocarbon group, to synthesize a β-hydrazino ester fixed to a resin represented by the following formula:

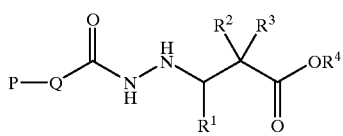

(III)

where P, Q, $R^1$, $R^2$, $R^3$ and $R^4$ have the same meanings as described above and then conducting cut out from the solid phase and cyclizing reaction, to synthesize pyrazolones represented by at least one of the following formulae (A) and (B)

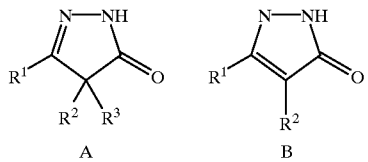

where $R^1$, $R^2$ and $R^3$ have the same meanings as described above.

PREFERRED EMBODIMENTS OF THE INVENTION

The present application provides and a hydrazone fixed to a resin which can be derived from a hydrazide fixed to a resin represented by the formula (I) and is represented by a formula (II) as defined in the first invention and the second invention described above, which enables solid phase synthesis method by Mannich type reaction and has not been known at all so far. In any of:

| Hydrazide fixed to a resin of the formula | (I) |
|---|---|
| P—Q—CO—NH—NH$_2$ | (I) |
| Hydrazone fixed to a resin of the formula | (II) |
| P—Q—CO—NH—N=CH—R$^1$ | (II), |

P represents a main chain of a resin polymer and Q represents a side chain bonded therewith in which the resin polymer constituting the main chain P may be an addition polymer, polycondensate, crosslinking product thereof, and, for example, addition polymer of alkenes having carbon-carbon doubles bonds or crosslinking polymers therefrom may be considered appropriate. Alkenes can include addition polymer or partial crosslinking product thereof of, for example, aliphatic olefins, aliphatic dienes, as well as α,β-aliphatic unsaturated carboxylic acids or esters thereof, α,β-aliphatic unsaturated nitriles, aromatic alkenes such as styrene, α-methylstyrene and divinyl benzene.

Various kinds of polyesters, epoxy resins, polyethers and polyamides as polycondensates may also be considered.

The side chain Q in this invention may include hydrocarbon chains which may have a substituent, or hydrocarbon chains which may have a substituent where an oxygen atom or nitrogen atom may intervene in the hydrocarbon chain as heteroatom, and the side chain Q may be formed together with the main chain: P or may be formed by grafting or pendant addition after forming the main chain P. In any of cases, the hydrocarbon chain may include various aliphatic groups, cycloaliphatic groups, aromatic groups and arylaliphatic groups and, for example, there can be mentioned alkylene chain represent by —(CH$_2$)$_n$—, a phenylene chain represented by —Ph—, and phenylene alkylene chain represented, for example, by —Ph—(CH$_2$)$_n$—, —(CH$_2$)$_n$—Ph—, —Ph—(CH$_2$)$_n$—Ph—. Alternatively, there can be also mentioned those bonded via heteroatom such as —Ph—O—Ph—, and —Ph—(CH$_2$)$_n$—O—Ph—.

The hydrocarbons may further contain various kinds of substituents which are not inhibitive to the solid phase synthesis reaction or further activate the reaction. There can be mentioned those substituents, for example, hydrocarbon groups such as alkyl group and aryl group, halogen atom, alkoxy group, acyloxy group, alkoxycarbonyl group, nitro group, cyano group and heterocyclic group.

Further, R$^1$ in the hydrazone fixed to the resin represented by the formula (II) is a hydrocarbon group or a heterocyclic group which may have a substituent where the hydrocarbon group may be linear or cyclic, saturated or unsaturated and aliphatic or aromatic, arylaliphatic and the heterocyclic group may also be various heterocyclic groups containing oxygen or nitrogen. Then, there can be mentioned various kinds of substituents not inhibitive to the solid phase synthesis reaction or further activating the reaction, for example, hydrocarbons such as alkyl group or aryl group, halogen atom, alkoxy group, acyloxy group, alkoxycarbonyl group, nitro group, cyano group and heterocyclic group.

The hydrazide fixed to the resin represented by the formula (I) can be produced by a method, for example, of carboxylating the resin polymer having the structure:

P—QH into a carboxylic acid resin:

P—Q—CO—OH esterifying the same and then reacting the ester with hydrazine.

The carboxylation is conducted, for example, in accordance with the method of Frechet, et al by reaction with BuLi and then reacting with CO$_2$. Of course, carboxylation is not restricted to this method. For the production of hydrazide fixed to the resin from the carboxylic acid resin, various modes may also be adopted for the reaction with hydrazide. For example, a carboxylic acid resin is esterified and then reacted with hydrazine mono-hydrate. The reaction may be conducted without using a solvent but use of 1,3-dimethyl-2-imidazolidinone (DMI) as the organic solvent is also effective. In addition, nitrile or nitrogen-containing heterocyclic compound such as pyridine or piperidine may also be mentioned.

The hydrazine mono-hydrate is used appropriately at a molar ratio of about 0.5 to 5 based on the carboxylic acid ester resin. The reaction temperature is at about 30 to 130° C. and, preferably, at about 60 to 110° C.

The hydrazone fixed to the resin of the formula (II) can be obtained by reacting the hydrazide fixed to the resin represented by the formula (I) with aldehydes represented by R$^1$CHO.

The reaction is conducted appropriately by using a solvent at a temperature of about 10 to 70° C., preferably, about 30 to 60° C. As the solvent, DMF, DMSO, nitriles, halogenated hydrocarbons or mixed solvent thereof with acetic acid may be mentioned as appropriate solvent.

The ratio of the aldehydes to the hydrazide fixed to the resin used for reaction is suitably within a molar ratio of 1 to 10.

The hydrazone fixed to the resin represented by the formula (II) can be used as a substrate for the solid phase Mannich type reaction. This reaction is conducted by reacting they hydrazone fixed to the resin of the formula (II) with the ketene silyl acetals of the formula (IV).

R$^2$–R$^4$ in the formula (III) is a hydrocarbon group or heterocyclic group which may have a substituent and can be selected from the same materials as R$^1$ in hydrazine fixed to the resin of the formula (II).

Further, R$^5$ may be any of aliphatic, aromatic or arylaliphatic hydrocarbon.

The solid phase reaction with the ketene silyl acetals described above can be conducted in a solvent by using a rare earth Lewis acid catalyst. The solvent can include, for example, halogenated hydrocarbon, aromatic hydrocarbon, ether, nitrile, alcohol and water, or an appropriate mixed solvent thereof.

The rare earth Lewis acid may be a compound of rare earth metals having Lewis acid property, which may be formed as organic acid ester salt, alcoholate, organic metal compound, organic complex compound and the like of scandium (Sc) and ytteribium (Yb), yttrium (Y), lanthanum (La), samarium (Sm), neodium (Nd). Among them, rare earth (OTf)$_3$, for example, Sc(OTf)$_3$ can be mentioned as more appropriate one.

The ratio of the ketene silyl acetals of the formula (III) to the hydrazone fixed to the resin of the formula (II) is generally from 0.5 to 10 molar ratio and, preferably, from 1 to 7 molar. The rare earth Lewis acid catalyst is used approximately at a molar ratio generally of 0.01 to 1 and, preferably, about 0.1 to 0.6.

The reaction temperature is suitably from −20 to 40° C. and, more preferably, at or near the room temperature.

The β-hydrazino ester of the formula (III) is obtained by the solid phase reaction described above in this invention.

The β-hydrazino ester provides an important means for constructing libraries of various kinds of nitrogen-containing organic compounds.

In this invention, pyrazolones represented by either one of the formulae (A) and (B) described above is synthesized by cutting out the β-hydrazino esters of the formula (III) from the resin and cyclizing the same.

The reaction can be conducted easily, for example, as a reaction with a metal alcoholate or a base using an alcoholic solvent. The alcoholate or the base is used, under a heating condition, at a molar ratio generally from 0.8 to 10 and, preferably, from 3 to 7 based on the β-hydrazino ester fixed to the resin.

By using various kinds of β-hydrazino esters fixed to the resin, libraries for various kinds of pyrazolones can be synthesized in a solid phase efficiently. The β-hydrazino esters fixed to the resin can be utilized for the synthesis to β-amino acids, β-lactams by cutting out from the resin, as well as the pyrazolones are also useful as intermediate products for the synthesis or medicines as physiologically active substances.

This invention will be explained more specifically with reference to the following examples.

EXAMPLES

Example 1

In accordance with the following reaction schemes, hydrazide fixed to a resin was formed, which was then reacted with an aldehyde to prepare a hydrazine fixed to the resin, and then pyrazolone was synthesized in a solid phase.

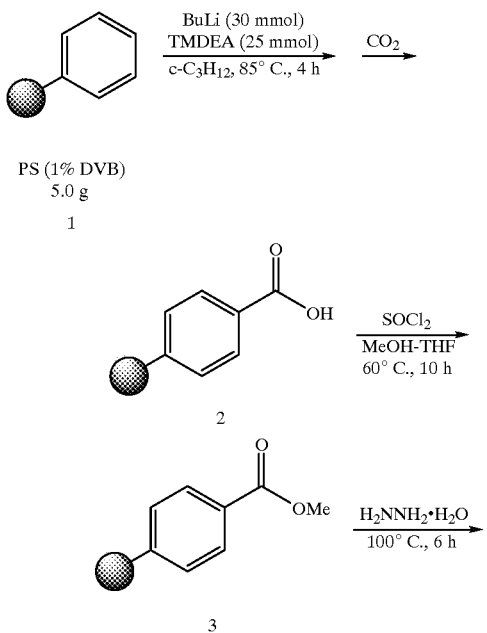

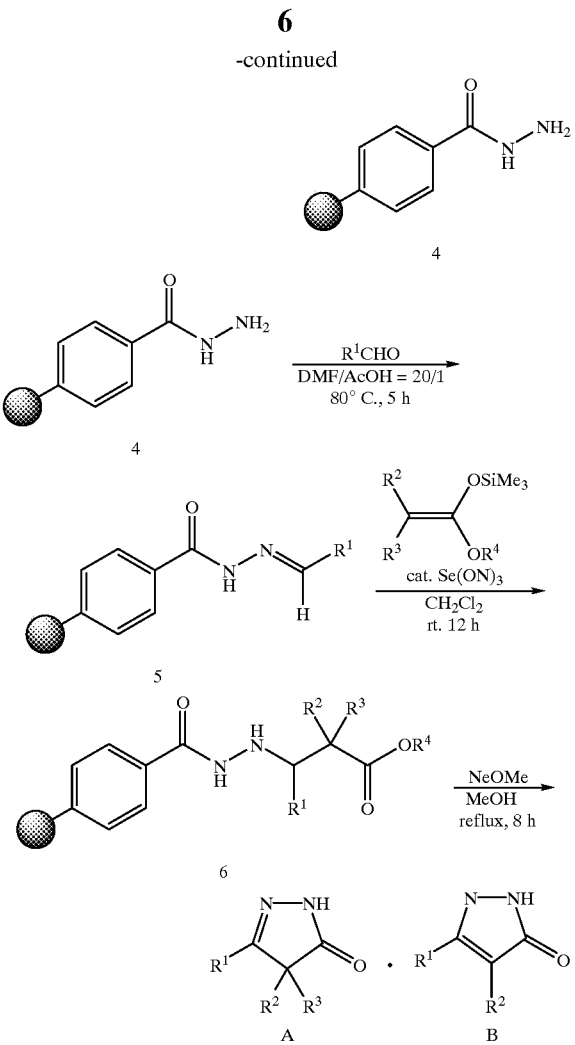

<1> Carboxylic Acid Resin

Under a room temperature, cyclohexane (40 ml) was added to polystyrene/divinyl benzene copolymer (1% crosslinked) (1) (200–400 mesh, approx., 5.0 g) manufactured by Aldrich Co., to which were added N,N,N',N'-tetramethyl ethylenediamine (4.0 ml, 25 mmol) and n-butyl lithium (1.54 M in hexane) (20 ml, 30 mmol). After stirring at 65° C. for 4 hours, the resin was separate by filtration, washed with cyclohexane for three times and a slurrified liquid mixture of $CO_2$—tetrahydrofuran was added. Successively, after washing with tetrahydrofuran; 1N hydrochloric acid (1:1) for three times, tetrahydrofuran for three times, water: tetrahydrofuran (1:1) for three times, water for three times water: tetrahydrofuran (1:1) for three times, tetrahydrofuran for three times and ether for five times, it was dried at a room temperature under a reduced pressure for 10 hours to obtain a carboxylic acid resin (2) (0.76 mmol/g).

<2> Methyl Ester Resin

Methanol (30 ml) was added to the carboxylic acid resin (2) prepared in (1) above (5.0 g) and after cooled to 0° C., thionyl chloride (8.0 ml, 109.6 mmol) and tetrahydrofuran (20 ml) were added. After elevating the temperature to 60° C. and stirring for 10 hours, the resin was separated by filtration and washed with methanol for three times, tetrahydrofuran for three times and ether for five times. When the product was dried at a room temperature under a reduced pressure for 10 hours, a methyl ester resin (3) (0.75 mmol/g) was obtained.

<3> Hydrazide Fixed to a Resin

Hydrazine mono-hydrate (20 ml) was added to the methyl ester resin (2.0 g) prepared in (2) above and after stirring at 100° C. for 6 hours, the resin was separated by filtration and washed with water for five times, water: dioxane (1:1) for three times, dioxane for three times and ether for five times. When the product was dried at a room temperature under a reduced pressure for 10 hours, an acyl hydrazine resin (4) (0.75 mmol/g) was obtained.

<4> Hydrazone Fixed to a Resin

N,N-dimethylformamide: acetic acid (20:1, 3.0 ml) was added to the acyl hydrazine resin fixed to the resin (4) prepared in <3> above (200.0 mg, 0.15 mmol) and, after adding an N,N-dimethylformamide solution (1.0 ml) containing 3-phenyl propion aldehyde (100.6 mg, 0.75 mmol/g), the temperature was elevated to 50° C. After stirring for 5 hours, the resin was separated by filtration and washed with N,N-dimethylformamide for three times, water for three times, tetrahydrofuran for three times and ether for five times. When the product was dried at a room temperature under a reduced pressure for 10 hours, an acyl hydrazone resin (5) in which $R^1 = -(CH_2)_2Ph$ (0.69 mmol/g) was obtained.

<5> β-hydrazino Ester Fixed to a Resin

Sc(III) (OTf)$_3$ (22.1 mg, 0.045 mmol) and methylene chloride (2.0 ml) were added to the acyl hydrazone resin (5) prepared in (4) above and, further, a methylene chloride solution (1.0 ml) containing ketene silyl acetal derived from methylisobutylate ester where $R^2$, $R^3$, $R^4$=Me (131.5 mg, 0.75 mmol) was added and stirred at a room temperature for 12 hours. The reaction was terminated by addition of a saturated aqueous solution of sodium hydrogen carbonate, the resin was separated by filtration and, after washing with methylene chloride for three times, tetrahydrofuran for three times, water for three times, tetrahydrofuran for three times and ether for five times, dried at a room temperature under a reduced pressure for 10 hours, β-hydrazino ester resin (6) where $R^2=-(CH_2)_2Ph$, $R^2$, $R^3$, $R^4$=Me (0.64 mmol/g) was obtained.

<6> Pyrazolone

Methanol (2.0 ml) and sodium methoxide (23.2 mg, 0.43 mmol) were added to the β-hydrazino ester resin prepared in <5> above (134.0 mg, 0.086 mmol) and stirred while heating under reflux for 8 hours. After adding amberlite (IRC-76) the resin was separated by filtration, the solvent was distilled off from the filtrate under a reduced pressure and when the residue was purified on thin film silica gel chromatography, pyrazolone (7) represented by the formula (A) where $R^1=-(CH_2)_2Ph$, $R^2$, $R^3$=Me (14.7 mg, 80%) was obtained.

Example 2

Various kinds of pylazolones were synthesized in the solid phase in the same procedures as those in Example 1.

The results are shown in Table 1.

TABLE 1

| entry | $R^1$ | $R^2$ | $R^3$ | $R^4$ | Yield (A/B) % |
|---|---|---|---|---|---|
| 1 | Ph(CH$_2$)$_2$ | Me | Me | Me | 80/— |
| 2 | C$_6$H$_{13}$ | Me | Me | Me | 88/— |
| 3 | (CH$_3$)$_2$CHCH$_7$ | Me | Me | Me | 67/— |
| 4 | Ph | Me | Me | Me | 38/— |
| 5 | Ph(CH$_2$)$_2$ | H | Me | Ph | —/38 |

Example 3

A carboxylic acid resin was produced by conducting Friedel-Crafts reaction using Ph(CH$_2$)$_4$COCl to polystyrene and then conducting AlCl$_3$—LAH reduction followed by carboxylation. By the same subsequent procedures as those in Example 1, pyrazolones were synthesized in the solid phase.

The results are shown in Table 2.

TABLE 2

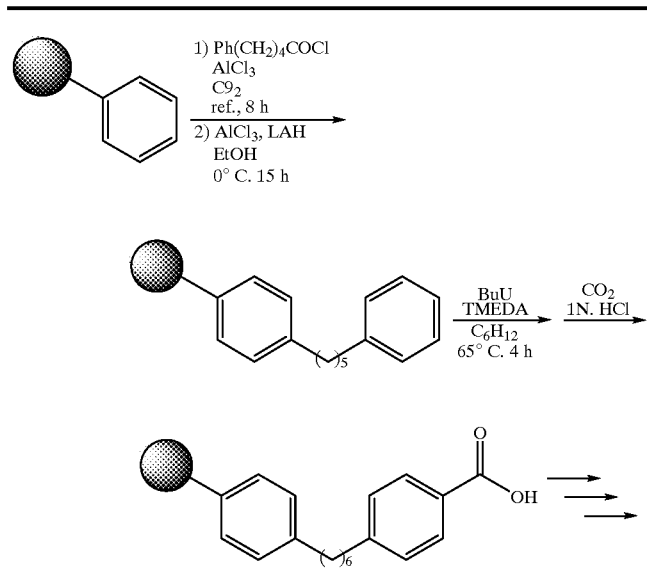

TABLE 2-continued

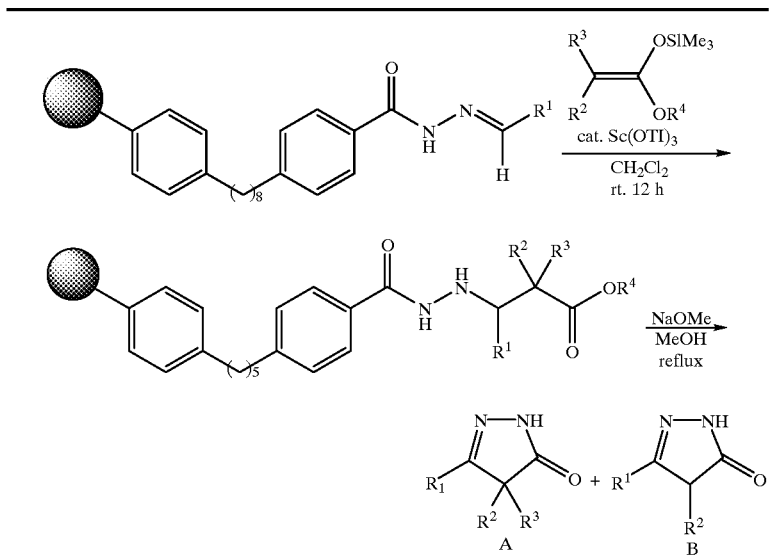

| entry | R¹ | R² | R³ | R⁴ | Yield (%) A / B |
|---|---|---|---|---|---|
| 1 | Ph(CH₂)₂ | Me | Me | Me | 77 (80)⁴ /+ |
| 2 | Ph(CH₂)₂ | Me | H | Ph | -/ 68 (38)⁵ |
| 3 | (CH₃)₂CHCH₂ | Me | H | Ph | -/ 62 (34)⁴ |
| 4 | C₆H₁₅ | Me | H | Ph | -/ 53 |

*Non-specer carboxylic resin was used.

Selectivity of pyrazolones (A) and (B) can be changed by changing the fixing resins, particularly, by introducing spacer hydrocarbon chains as shown in Table 2.

Physical properties of the pyrazolones synthesized in Examples 1 to 3 above are shown below.

TABLE 3

3-Heptyl-4,4-dimethyl-2-pyrazolin-5-one

¹HNMR δ 0.90(t, 3H, J=6.6Hz). 1.20–1.39(m, 4H), 1.23(s, 6H), 1.63–1.70(m, 2H), 2.29(t, 2H, J=7.6Hz), 8.35(s, 1H); ¹³CNMR δ 14.0, 20.9, 22.5, 25.2, 27.6, 29.1, 31.6, 47.4, 168.6, 181.0

3-(2'-Phenylethyl)-4-methyl-3-pyrazolin-5-one

¹HNMR δ 1.25(s, 1H), 1.81(s, 3H), 2.85(brs, 4H), 7.12–7.29(m, 5H); ¹³CNMR δ 29.7, 31.0, 33.8, 91.2, 126.5, 128.4, 128.7, 140.1, 140.4

3-Isobutyl-4-methyl-3-pyrazolin-5-one

¹HNMR δ 0.91(d, 6H, J=6.6Hz), 1.26(s, 1H), 1.85–1.92(m, 4H), 2.36(d, 2H, J=6.6Hz), 7.38(brs, 1H); ¹³CNMR δ 6.1, 22.1, 28.2 33.9, 96.9, 141.4, 161.2

3-Heptyl-4-methyl-3-pyrazolin-5-one

¹HNMR δ 0.88(Brs, 3H), 1.25–1.28(m, 6H), 1.57(brs, 2H), 1.87(brs, 3H), 2.49(Brs, 2H)

As has been explained specifically above, synthesis of Pyrazolones by the application of the Mannich type reaction on the solid phase synthesis is enabled by this invention, and the pyrazolones can efficiently construct libraries.

What is claimed is:

1. β-hydrazino ester fixed to a resin represented by the following formula (III):

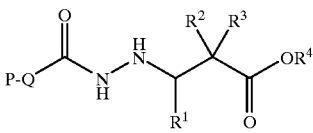

where P represents a main chain of a resin polymer, Q represents a hydrocarbon side chain optionally having a substituent which may be boned via a heteroatom, R¹, R², R³ and R⁴ each represents a hydrocarbon group or a heterocyclic group optionally having a substituent.

2. A production process for a β-hydrazino ester fixed to a resin as defined in claim 3, wherein the process comprises reacting a hydrazone fixed to a resin represented by the following formula:

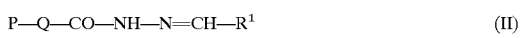

where P represents a main chain of a resin, Q represents a hydrocarbon side chain optionally having a substituent which may be boned via a heteroatom and R¹ represents a hydrocarbon group or a heterocyclic group optionally having a substituent, with a ketene silyl acetal represented by the following formula:

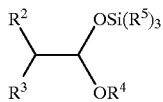

(IV)

where $R^2$, $R^3$ and $R^4$ each represents a hydrocarbon group or a heterocyclic group which may have a substituent and $R^6$ represents a hydrocarbon group.

3. A method of synthesizing pyrazolones which comprises reacting a hydrazone fixed to a resin represented by the following formula:

(II)

where P represents a main chain of a resin, Q represents a hydrocarbon side chain optionally having substituent which may be bonded via a heteroatom and $R^1$ represents a hydrocarbon group or a heterocyclic group optionally having a substituent, with ketene silyl acetals represented by the following formula:

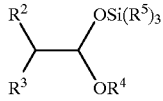

(IV)

where $R^2$, $R^3$ and $R^4$ each represents a hydrocarbon group or a heterocyclic group which may have a substituent respectively and $R^6$ represents a hydrocarbon group, to synthesize a β-hydrazino ester fixed to a resin represented by the following formula:

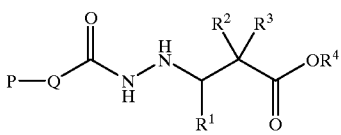

(III)

where P, Q, $R^1$, $R^2$, $R^3$ and $R^4$ have the same meanings as described above, which is then cut out from the solid phase and put to cyclizing reaction, to synthesize pyrazolones represented by at least one of the following formulae (A), (B)

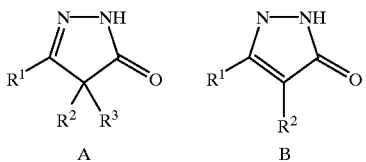

where $R^1$, $R^2$ and $R^3$ have the same meanings as described above.

* * * * *